United States Patent
Eaton

(10) Patent No.: US 9,545,501 B2
(45) Date of Patent: Jan. 17, 2017

(54) SYSTEM FOR A WIRE-LUMEN FREE BALLOON CATHETER

(71) Applicant: Cook Medical Technologies LLC, Bloomington, IN (US)

(72) Inventor: Elizabeth A. Eaton, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 4 days.

(21) Appl. No.: 14/196,859

(22) Filed: Mar. 4, 2014

(65) Prior Publication Data

US 2014/0257182 A1    Sep. 11, 2014

Related U.S. Application Data

(60) Provisional application No. 61/773,570, filed on Mar. 6, 2013.

(51) Int. Cl.
| | | |
|---|---|---|
| *A61M 29/00* | (2006.01) | |
| *A61M 25/01* | (2006.01) | |
| *A61M 25/09* | (2006.01) | |
| *A61M 25/10* | (2013.01) | |

(52) U.S. Cl.
CPC ..... *A61M 25/0172* (2013.01); *A61M 25/0905* (2013.01); *A61M 25/10* (2013.01); *A61M 2025/1093* (2013.01)

(58) Field of Classification Search
CPC .............. A61M 25/0172; A61M 25/10; A61M 2025/1093; A61M 25/0905
See application file for complete search history.

(56) References Cited

U.S. PATENT DOCUMENTS

| 4,827,941 A | * | 5/1989 | Taylor ............... | A61M 25/0905 140/111 |
|---|---|---|---|---|
| 4,875,489 A | | 10/1989 | Messner et al. | |
| 4,966,163 A | | 10/1990 | Kraus et al. | |
| 5,191,888 A | * | 3/1993 | Palmer .............. | A61M 25/0905 600/434 |
| 5,195,535 A | | 3/1993 | Shank | |
| 5,267,573 A | | 12/1993 | Evans et al. | |
| 5,271,415 A | | 12/1993 | Foerster et al. | |
| 5,404,888 A | * | 4/1995 | Kontos ............. | A61M 25/0905 600/585 |
| 5,421,348 A | | 6/1995 | Larnard | |
| 5,513,650 A | * | 5/1996 | Johansen .......... | A61M 25/0905 600/508 |
| 6,039,700 A | | 3/2000 | Sauter | |
| 6,451,026 B1 | | 9/2002 | Biagtan et al. | |
| 6,685,653 B2 | | 2/2004 | Ehr et al. | |
| 7,815,599 B2 | | 10/2010 | Griffin et al. | |
| 2002/0072705 A1 | * | 6/2002 | Vrba ...................... | A61F 2/958 604/96.01 |

(Continued)

*Primary Examiner* — Jing Ou
(74) *Attorney, Agent, or Firm* — Brinks Gilson & Lione

(57) ABSTRACT

The invention relates to a low profile lumen free balloon catheter and a system for advancing the lumen free balloon from a build wire to a wire guide. The low profile balloon lacks an internal wire guide cannula between the catheter shaft and the soft tip. A releasable engagement is provided to connect/disconnect the build wire to/from the wire guide. A soft tip seals around the wire guide following advancement of the balloon catheter over the wire guide.

16 Claims, 5 Drawing Sheets

(56) References Cited

U.S. PATENT DOCUMENTS

| | | | |
|---|---|---|---|
| 2002/0082549 A1* | 6/2002 | Duchamp | A61M 25/1034 604/96.01 |
| 2003/0028127 A1* | 2/2003 | Balzum | A61M 25/0905 600/585 |
| 2003/0032920 A1* | 2/2003 | Wantink | A61M 25/001 604/103 |
| 2003/0125761 A1* | 7/2003 | Meens | A61F 2/958 606/192 |
| 2006/0271090 A1* | 11/2006 | Shaked | A61B 17/12022 606/192 |
| 2007/0167972 A1* | 7/2007 | Euteneuer | A61M 25/09 606/192 |
| 2007/0282367 A1* | 12/2007 | Jeffrey | A61F 2/958 606/194 |
| 2008/0004568 A1* | 1/2008 | Jeffrey | A61M 25/0069 604/96.01 |
| 2008/0262470 A1 | 10/2008 | Lee et al. | |

* cited by examiner

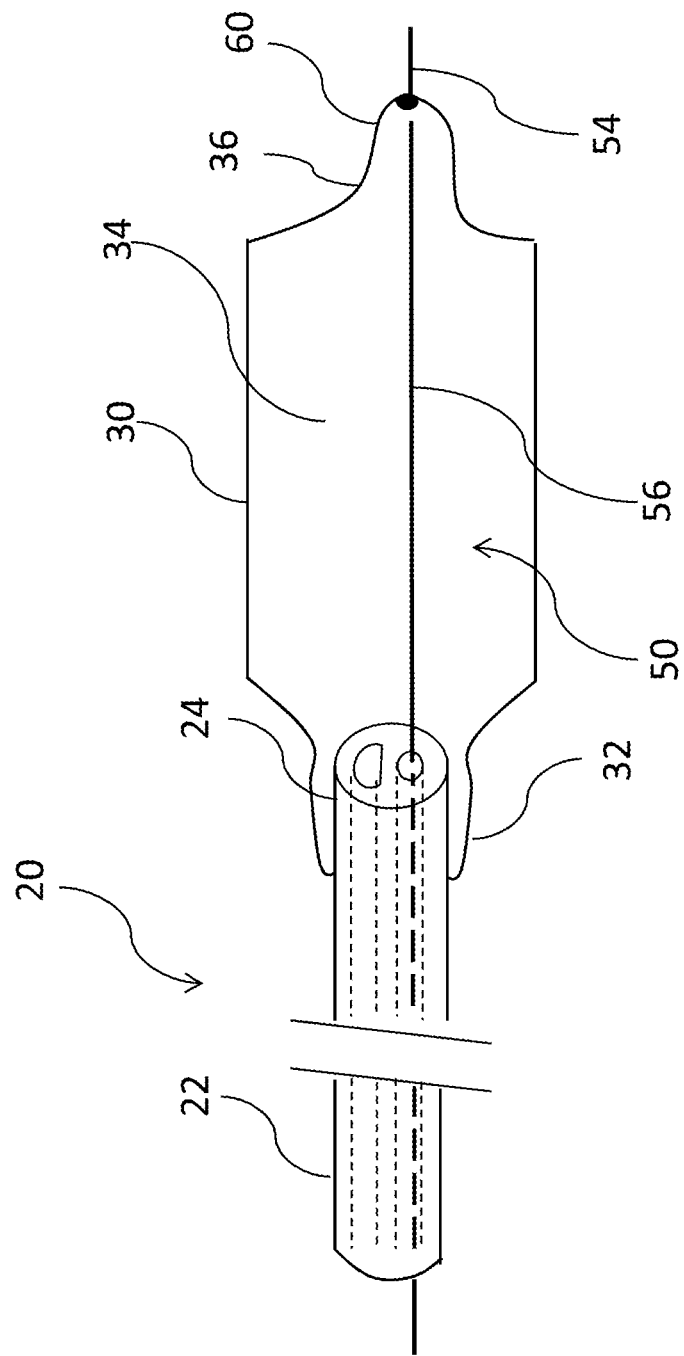

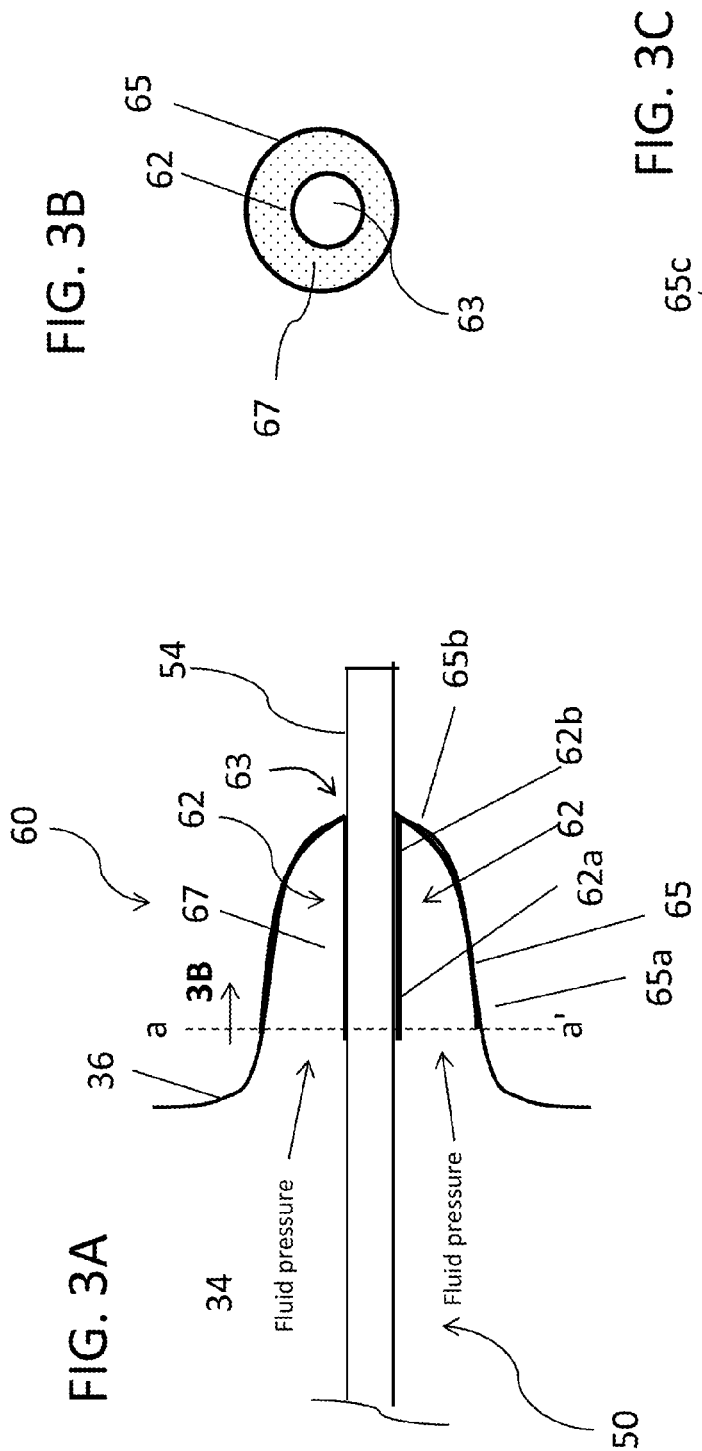
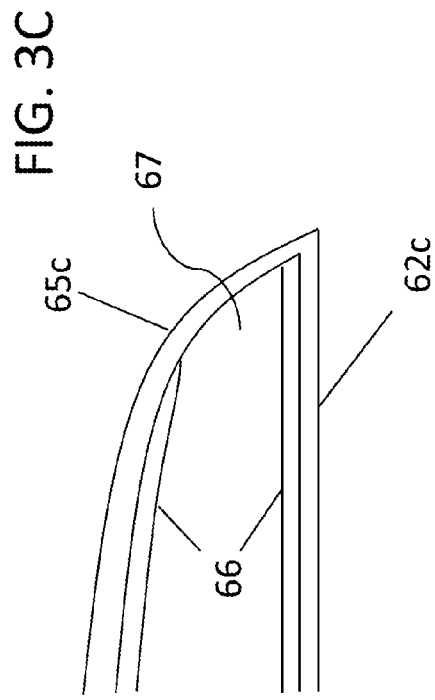

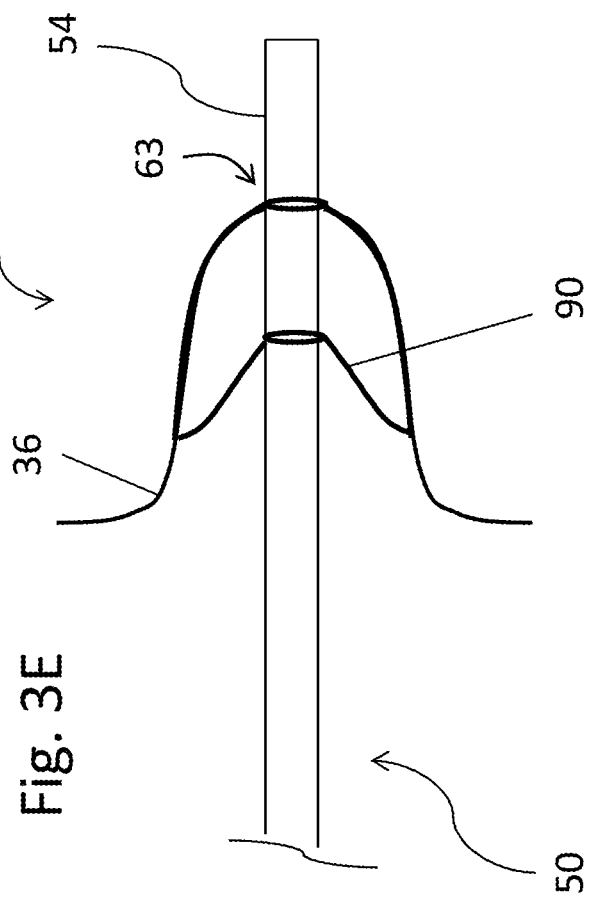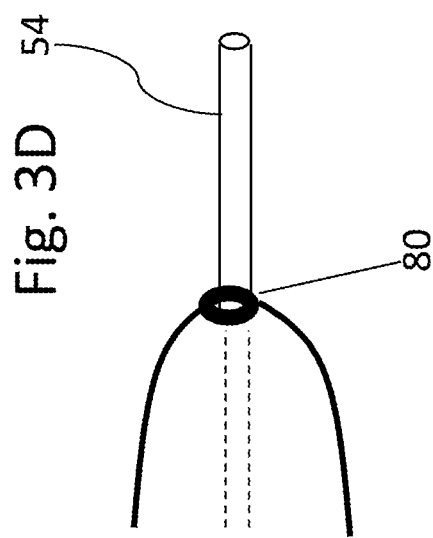
Fig. 3D
Fig. 3E

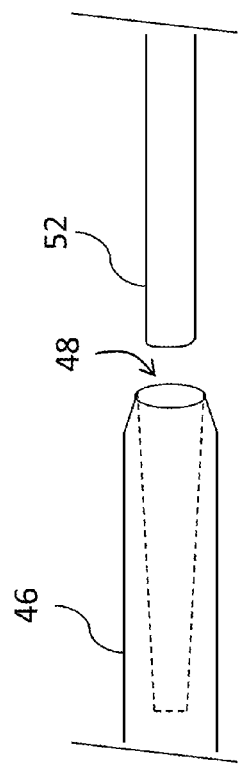
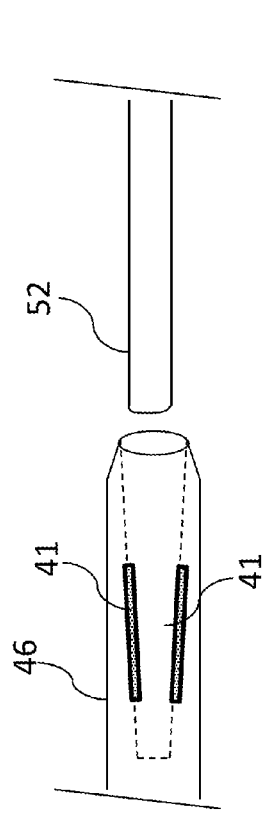
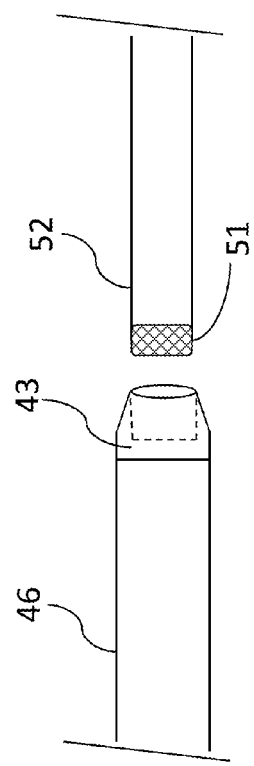
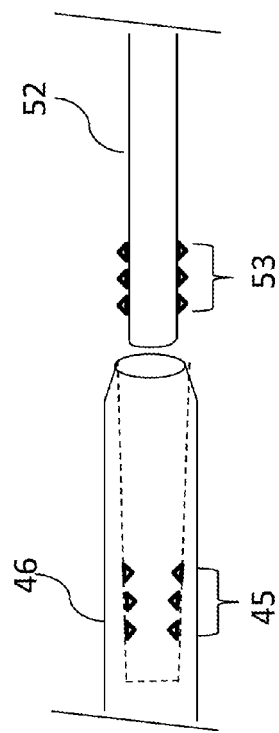
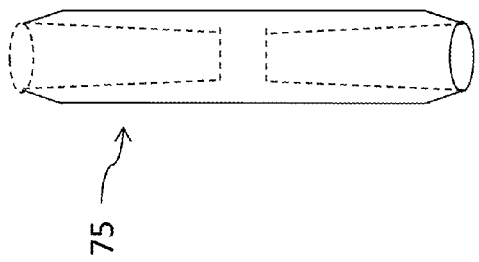
Fig. 4A
Fig. 4B
Fig. 4C
Fig. 4D
Fig. 4E

SYSTEM FOR A WIRE-LUMEN FREE BALLOON CATHETER

RELATED APPLICATIONS

The present patent document claims the benefit of the filing date under 35 U.S.C. §119(e) of Provisional U.S. Patent Application Ser. No. 61/773,570, filed Mar. 6, 2013, which is hereby incorporated by reference.

TECHNICAL FIELD

The present invention relates to wire-lumen free balloon catheter systems and systems for advancing a wire-lumen free balloon catheter from a build wire onto a wire guide. The absence of the internal wire guide lumen gives the balloon catheter a low profile, making it suitable for applications calling for a smaller diameter balloon catheter.

BACKGROUND OF THE INVENTION

Wire guides are frequently used to position medical devices, such as balloon catheters, at a desired location in a patient's body (e.g., the vascular system). In a typical procedure, a wire guide is first inserted into a body lumen and steered into position followed by advancing a balloon catheter over the wire guide to the desired treatment site.

Typical balloon catheters are composed of an elongated shaft with an inflatable balloon portion attached to the distal end of the elongated shaft. The shaft typically has multiple lumens, one being an inflation lumen for the balloon and another serving as a wire guide lumen to allow the catheter and shaft to be advanced over a wire guide that has already been positioned in a patient. The elongated shaft of one type of typical balloon catheter terminates just inside the proximal end of the balloon, where a second, smaller single lumen shaft/cannula is bonded onto the main shaft and extends through the interior of the balloon in order to preserve the wire guide lumen through to the distal end of the balloon. The presence of the smaller shaft within the balloon allows the balloon to initially be mounted on the proximal end of the wire guide and advanced over the wire guide without the wire guide poking and damaging the balloon material.

The smaller wire guide shaft within the balloon may be about 0.050" in outer diameter in order to accommodate a wire guide of about 0.035" outer diameter. The presence of the smaller shaft in the interior of the balloon, however, adds to the overall dimensions of the balloon, thus limiting the use of the balloon catheter in applications requiring a still lower profile balloon. Thus, there exists a need for lower profile balloons and systems for advancing lower profile balloons onto wire guides that have already been positioned in a patient.

SUMMARY OF THE INVENTION

One aspect of the invention provides a system for advancing a low profile balloon from a build wire onto a wire guide. The balloon has a low profile by reason of the total absence of a shaft or cannula in the internal cavity of the balloon. In one aspect, the system includes a build wire and a balloon catheter mounted on the build wire. In one embodiment the invention provides a wire guide where the proximal end of the wire guide and the distal end of the build wire are designed to form a releasable engagement allowing the low profile balloon to be advanced from the build wire over the point of engagement onto the wire guide without puncturing or poking the material of the balloon. In another aspect, the invention provides a low profile balloon mounted on a wire guide where the balloon lacks an internal shaft or cannula for the wire guide. The systems of the invention also include a soft tip attached to the distal neck of the balloon. Various arrangements also allow the soft tip to form a seal around the wire guide.

BRIEF DESCRIPTION OF THE DRAWINGS

FIG. 2 illustrates a side view of the system for advancing a low profile balloon catheter after the balloon has been advanced over the wire guide. The balloon portion is shown in a cut away view to show the wire guide and interior of the balloon.

FIG. 3A shows a side cut-away view of one embodiment of a soft tip forming a seal around a wire guide.

FIG. 3B illustrates a cross-sectional view of the soft tip in FIG. 3A along the line a-a' facing distally.

FIG. 3C illustrates a partial close-up view of an embodiment of a soft tip co-extruded with a higher melting liner.

FIG. 3D illustrates a perspective view of a soft tip and seal arrangement around a wire guide.

FIG. 3E illustrates a partial perspective view of an embodiment of the soft tip forming an inner seal around a wire guide.

FIG. 4A illustrates a perspective close-up view of one embodiment of a releasable engagement between the distal end of a build wire and the proximal end of a wire guide.

FIG. 4B illustrates a close-up view of an embodiment of a releasable frictional engagement between the distal end of a build wire and the proximal end of a wire guide.

FIG. 4C illustrates a close-up view of one embodiment of a releasable magnetic engagement between the distal end of a build wire and the proximal end of a wire guide.

FIG. 4D illustrates a close-up view of one embodiment of a releasable threaded engagement between the distal end of a build wire and the proximal end of a wire guide.

FIG. 4E illustrates a close-up view of one embodiment of a connector to join a build wire with a wire guide.

DETAILED DESCRIPTION

Figure 1:
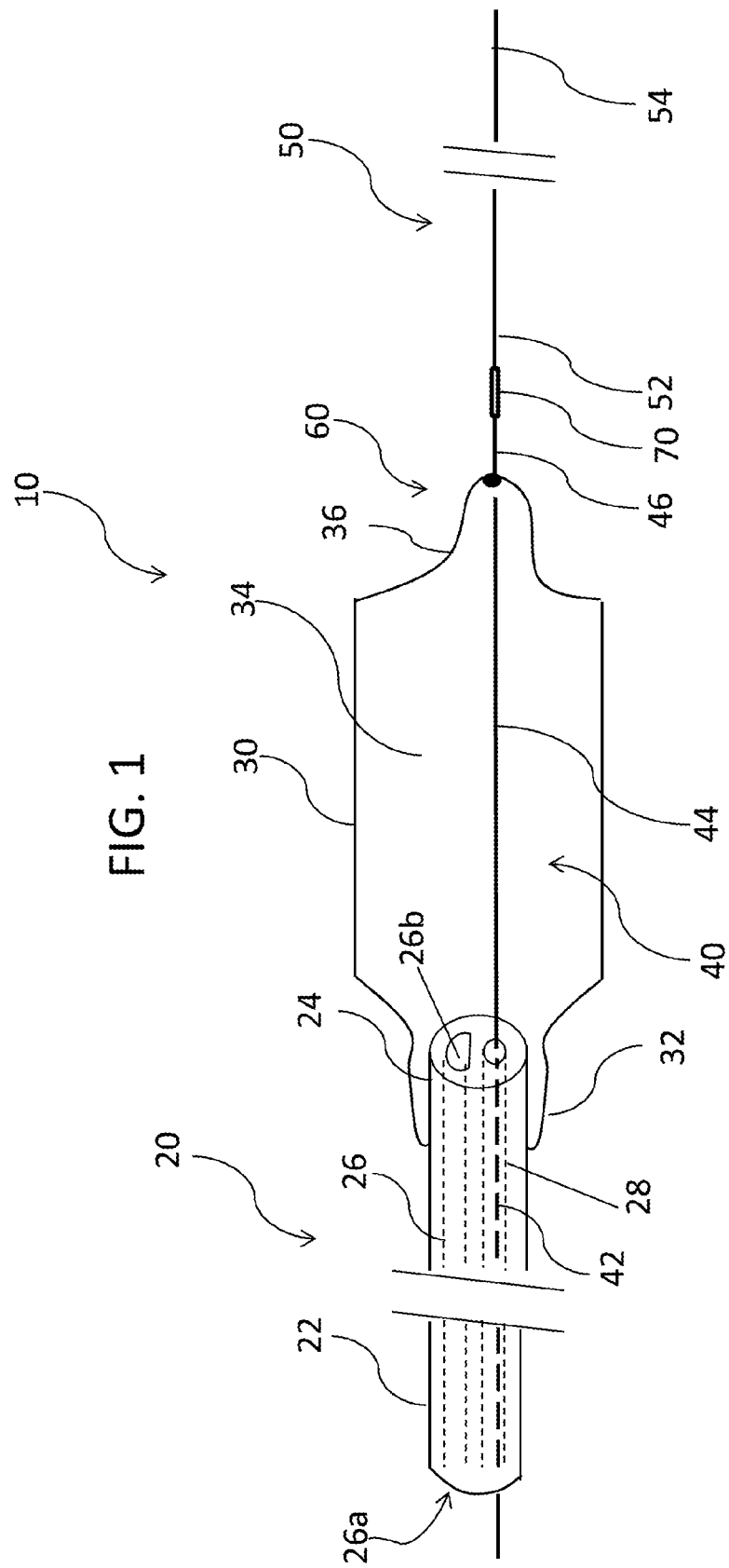
FIG. 1 illustrates a side view of the system for advancing a low profile balloon catheter as positioned prior to advancement of the balloon over the wire guide. The balloon portion is shown in a cut away view to show the build wire and interior of the balloon.

The present invention is not limited to those embodiments described herein, but rather, the disclosure includes all equivalents including those of different shapes, sizes, and configurations, including but not limited to, other types of balloon catheters. The devices and methods may be used in any field benefiting from a balloon catheter. Additionally, the devices and methods are not limited to being used with human beings, others are contemplated, including but not limited to, animals.

Unless otherwise defined, all technical and scientific terms used herein have the same meaning as commonly understood by one of ordinary skill in the art. In case of conflict, the present document, including definitions, will control. Preferred methods and materials are described below, although systems, apparatuses, methods, and materials similar or equivalent to those described herein can be used in practice or testing. The systems, materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of" and "consisting essentially of," the embodiments or elements presented herein, whether explicitly set forth or not.

The term "proximal," as used herein, refers to a direction that is generally towards a physician during a medical procedure.

The term "distal," as used herein, refers to a direction that is generally towards a target site within a patient's anatomy during a medical procedure.

FIG. 1 illustrates one embodiment of the system 10 for advancing a low profile balloon catheter from a build wire onto a wire guide. The system includes an elongated shaft 20, a balloon 30, a build wire 40, a wire guide 50, a soft tip 60 and an optional releasable engagement 70. The embodiment of FIG. 1 illustrates an over-the-wire type design for the balloon catheter, however, the system of the invention is also suitable for use with balloon catheters of the rapid- or peripheral-exchange type.

The balloon 30 has a proximal portion 32 that is bonded or connected to the elongated shaft 20 at the distal end 24. For example, the proximal neck 32 may be bonded to the distal end 24 of the shaft with two or more pieces of PEEK or similar material used to keep the lumens open during the bonding process. The balloon has a distal neck 36 that is bonded to a soft tip 60. The balloon and soft tip together have an internal cavity 34. Any small portion of the distal end 24 of the elongated shaft 20 is not considered to be within the "internal cavity" as used herein. In an alternate embodiment, the balloon is fabricated such that the balloon material itself forms the soft tip. This simply makes the soft tip a part of the distal part of the balloon, rather than a separate structure bonded to the balloon neck.

The elongated shaft 20 has a proximal end 22 and a distal end 24. A fluid supply lumen 26 extends along the longitudinal axis of the shaft 20 and communicates with the interior cavity 34 of the balloon and soft tip through the distal opening 26b. Fluid may be supplied to the balloon cavity 34 from a fluid supply system through the proximal opening 26a, the fluid supply lumen 26, and the distal opening 26b. The shaft 20 also has a wire guide lumen 28 to accommodate the build wire 40 or the wire guide 50. Although the catheter shaft in FIG. 1 is shown with a fluid supply lumen adjacent a wire guide lumen, the invention is not limited to the particular catheter type shown in the Figures. For example, the system may also include a multi-lumen catheter or a coaxial catheter. In an alternative arrangement, the fluid supply lumen may also function as the wire guide lumen, thereby eliminating the necessity of a separate lumen.

A build wire 40 has a first portion 42 disposed within the wire guide lumen 28 of the elongated shaft and a second portion 44 disposed within the internal cavity of the balloon and soft tip. The distal end 46 of the build wire projects through the end of the soft tip 60. The distal end of the build wire can form a releasable engagement with the proximal end 52 of the wire guide 50. The releasable engagement may be a separate structural element 70 as illustrated in FIG. 1. Alternatively, the releasable engagement may result from a direct connection between the distal end 46 and the proximal end 52 as shown in FIGS. 4A-4D and as explained hereinbelow.

The balloon 30 lacks an internal wire guide shaft or cannula. Thus, the second portion 44 of the build wire directly contacts any fluid supplied to the internal cavity 34. The absence of an internal wire guide gives the balloon 30 a lower profile and greater flexibility since it lacks the additional bulk of a wire guide shaft that is present in conventional balloons.

When the balloon and soft tip are filled with a first fluid volume (e.g., a liquid or a gas), the internal cavity of the balloon and soft tip holds a first balloon volume, which consists of the volume of the second portion of the build wire (i.e., the build wire volume) plus the first fluid volume.

In operation, a user would first achieve access and correct position inside the patient with a wire guide and then connect the proximal end of the wire guide to the distal end of the build wire. At this point, the first and second portions of the build wire would already be disposed within the elongated shaft and the balloon cavity respectively. The balloon would then be advanced over the releasable engagement and onto the wire guide into an appropriate position at a selected treatment site. FIG. 2 illustrates the positioning of the balloon 30 over the wire guide following this advancement step. Once the balloon has been fully deployed onto the wire guide, the build wire may be disconnected and removed. After advancing the balloon over the wire guide, a portion of the wire guide 56 is positioned within the internal cavity 34 with the distal tip 54 projecting through the soft tip 60. This system for advancing a balloon without a separate internal wire guide shaft allows the balloon to be advanced without the risk of poking and damaging the balloon material with the wire guide during the process of advancing the balloon. The build wire, in effect, draws the wire guide safely through the balloon cavity without the need for the separate wire guide shaft inside the balloon.

A "build wire" according to the invention includes any metallic or non-metallic wire, string, thread, cable, cord, chain, fiber, etc. capable of extending through the elongated shaft through the balloon cavity and out the distal end of the soft tip and capable of being exchanged for a wire guide or another build wire. The term "build wire" refers to any of the foregoing structures from which a balloon catheter may be advanced onto another wire, such as a wire guide that has been disposed within a patient. Alternatively, during manufacturing, one may swap a first build wire for a second build wire. Or for shipping purposes, a build wire may be swapped with a shipping wire (i.e., a third build wire). It may be desirable to swap wires during manufacturing and shipping for reasons of cost or ease of manufacture (e.g., better heat conductivity in bonding). The different build wires, whether first, second, third, etc. are referred to herein as a build wire for simplicity. Typically a build wire is exchanged with another wire using a releasable engagement between the two wires as described herein. In some circumstances, however, it may be possible to exchange a build wire with a second wire by carefully sliding a second wire against the distal tip of the build wire and pushing the build wire back out of the balloon cavity with the second wire. Care must be taken during this operation to avoid puncturing the balloon material. The various build wires are not limited to a particular diameter but may be adjusted in size to suit the particular application.

Once the balloon has been positioned over the wire guide, the balloon and soft tip may be filled with a second fluid volume, resulting in the internal cavity of the balloon and soft tip holding a second balloon volume. Since the portion of the wire guide 56 inside the internal cavity has its own volume, the second balloon volume consists of the volume of the wire guide (i.e., the wire guide volume) plus the second fluid volume.

To prevent leakage of the second fluid volume from the distal end of the soft tip, the invention provides for a sealing engagement of the soft tip with the wire guide. One embodiment of a sealing mechanism for the soft tip and wire guide is illustrated in FIGS. 3A and 3B. In the embodiment of FIG. 3A, the soft tip 60 has an inner sleeve 62 and an outer tubing 65 where the distal end 62b of the inner sleeve is bonded to the distal end 65b of the outer tubing. The outer tubing may be cut slightly shorter than the inner sleeve and the two heat bonded at the distal ends. The proximal end 62a of the inner sleeve and the proximal end 65a of the outer tubing terminate at the distal balloon neck 36, where a bond is formed between the balloon neck and the outer tubing. Bonding of the distal ends 62b and 65b forms an annular cavity 67 that is in fluid communication with the balloon cavity 34. Fluid supplied to the balloon cavity fills the annular cavity 67 with fluid pressure providing the sealing force to seal the inner sleeve against the wire guide and thus prevent leakage. This mechanism operates similarly to a Heimlich valve or flutter valve. A lumen 69 extends through the inner sleeve 62 to accommodate the wire guide, which projects beyond the distal opening 63 of the soft tip.

In an alternative sealing engagement mechanism, the distal tip of the soft tip is a seal 80 formed from a soft material such as silicone (FIG. 3D). The seal 80, however, is not limited to silicone and may include a seal made of any suitable materials well known to those skilled in die art.

The seal may function like a silicone check-flow valve or hemostatic valve that allows the build wire and wire guide to pass through the distal opening 63 of the soft tip while sealing around the wire guide to prevent leakage of fluid supplied to the balloon cavity. The seal 80 may be co-extruded with the soft tip material or bonded to the distal tip of the soft tip.

In yet another embodiment shown in FIG. 3E, the soft tip is configured with an inner flap 90 that extends into the interior of the soft tip from the point of bonding of the soft tip to the distal balloon neck. The inner flap 90 is formed around substantially the entire 360° circumference of the interior of the soft tip and sized such that the opening in the flap is sufficiently small to fit snugly around the wire guide. Alternatively, multiple flaps may be used to function in the same manner as the single flap shown in FIG. 3E. The multiple flaps may meet or overlap so as to cooperatively surround the wire guide. The flaps may be oriented perpendicular to the wire or some combination of perpendicular and parallel. The flaps may be sized to collapse inward as far as the wire and any additional material rests against the wire in parallel with it. When the balloon fills with a fluid, the inner flap prevents leakage of fluid from the distal end of the balloon and soft tip.

The soft tip may be manufactured from a variety of polymeric materials such as, for example, nylon, polyethylene, polyvinyl chloride, polyesters, polyamides, polyimides, polyurethanes, high density polyethylene, polytetrafluoroethylene, and composite materials. In the case of the embodiment shown in FIG. 3A, the inner sleeve 62 and the outer tubing 65 may be co-extruded with a material of higher melting point. FIG. 3C illustrates an embodiment where the soft tip is co-extruded with a higher melting material to form the inner layers/liners 66. The outer layers 62c and 65c, which are of a lower melting material, heat bond with each other and with the distal balloon neck 36. The inner layers 66, however, resist melting and thus do not melt together. This allows the soft tip to maintain the annular cavity 67 open to receive fluid pressure as described above.

The releasable engagement between the distal end of the build wire and the proximal end of the wire guide may be accomplished in a variety of ways. FIGS. 4A-E illustrate just several possible ways in which a releasable engagement may be achieved. FIG. 4A illustrates a general design according to one embodiment where the distal end of the build wire has a tapered bore hole 48 into which the proximal end 52 of the wire guide may be inserted. In the embodiment shown in FIG. 4B, a fictive surface in the interior of the bore hole provides a frictional engagement. The fictive surface may be a roughened surface, a soft (grabby) material, or an adhesive coating. A user would insert the proximal end of the wire guide into the bore hole in the build wire and create a press fit that would hold sufficiently to draw the wire guide through the balloon and into the shaft. In the event that the wire guide is made of a magnetic material, a magnet placed at the distal tip of the build wire may be used to form a releasable engagement. FIG. 4C illustrates one embodiment having a magnet 43 at the distal end of the build wire and a magnetic material 51 at the proximal end of the wire guide. Alternatively, the position of the magnet could be reversed. As still another type of releasable engagement, the distal end of the build wire and the proximal end of the wire guide may be threaded to provide a threaded engagement. FIG. 4D illustrates one embodiment where the bore hole at the distal end is provided with threads 45 that can mate with the threads 53 at the proximal end of the wire guide. The threaded engagement allows a user to screw the build wire over the wire guide. Alternatively, a quick-release type mechanism could be employed to mate up the build wire with the wire guide.

In another embodiment (not shown), the bore hole may be sufficiently long to allow the wire guide to push into the build wire and drive it back out of the balloon catheter. This method would be particularly suitable for catheters where the wires exit the shaft after a relatively short distance (e.g., rapid- or peripheral-exchange catheters).

In still another variation, the releasable engagement may be achieved with an independent coupler 75 (FIG. 4E) that joins both the distal end of the build wire and the proximal end of the wire guide. Coupler 75 may employ any of the foregoing engagement mechanisms described above in conjunction with FIGS. 4A-D. Other mechanisms for coupling wire guides to extension wires are well known in the art and would also be suitable for achieving a releasable engagement suitable for advancing a low profile balloon catheter according to the invention from a build wire onto a wire guide.

The embodiments shown in FIGS. 4A-D show a build wire with a tapered outer diameter at the distal end. Although a taper is not required, it provides a smoother transition for the advancing balloon from the build wire to the wire guide.

The build wire may have a slightly larger diameter in order to accommodate the wire guide in the bore hole at the distal end of the build wire. The roles of the distal end of the build wire and the proximal end of the wire guide may, however, be reversed so that the wire guide has a slightly larger diameter allowing the bore hole to be located in the proximal end of the wire guide instead. Employing a wire guide with a slightly larger diameter may provide for a tighter seal with the distal end of the soft tip. The diameters of the build wire and wire guide may also be varied along their lengths. For example, the distal end of the build wire and the proximal end of the wire guide may be manufactured with a small diameter to enable a corresponding reduction in the profile of the releasable engagement (e.g., connector 75).

The lumen-free balloon and build wire arrangement may be manufactured as follows. The proximal balloon neck may be bonded to the distal end of the shaft with polyether ether ketone (PEEK) to hold open the lumens of the shaft. Either before or after bonding of the shaft with the balloon, a build wire is inserted through the wire lumen of the shaft and extending out the distal end of the shaft sufficiently to pass the distal neck of the balloon and eventual soft tip. The soft tip is bonded to the distal balloon neck either butt-welded or bonded over the build wire to the inside of the balloon neck. Although the build wire may need to move slightly to accommodate some processes, the build wire should be maintained through the soft tip to avoid accidental damage to the balloon itself (e.g. poking). In bonding the soft tip to the distal balloon neck, PEEK or other heat-resistant sleeve may be placed over the build wire if needed.

In some embodiments, the balloon catheter system may include one or more components configured to aid in visualization and/or adjustment during implantation, repositioning, or retrieval. For example, the system may include one or more radiopaque markers configured to provide for fluoroscopic visualization for accurate deployment and positioning. Radiopaque markers may be affixed (e.g., by welding, gluing, suturing, or the like) on the balloon, the shaft, the build or shipping wire, on an optional stent, or on the soft tip.

Those of skill in the art will appreciate that embodiments not expressly illustrated herein may be practiced within the scope of the present discovery, including that features described herein for different embodiments may be combined with each other and/or with currently-known or future-developed technologies while remaining within the scope of the claims presented here. It is therefore intended that the foregoing detailed description be regarded as illustrative rather than limiting. Furthermore, the advantages described above are not necessarily the only advantages of the discovery, and it is not necessarily expected that all of the described advantages will be achieved with every embodiment of the discovery.

What is claimed is:

1. A system for advancing a low profile balloon catheter onto a wire guide comprising:
   (a) a balloon catheter arrangement comprising
      (i) an elongate shaft having a fluid supply lumen, a proximal end, and a distal end;
      (ii) a balloon having an internal cavity, a proximal portion and a distal neck, the proximal portion of the balloon being mounted on the distal end of the elongate shaft; and
      (iii) a soft tip having a proximal end, a distal end, and a distal opening, wherein the proximal end of the soft tip is joined to the distal neck of the balloon, the soft tip further comprising an inner sleeve having a proximal end and a distal end; and an outer tubing having a proximal end and a distal end, the proximal end of the outer tubing being bonded to the distal neck of the balloon, the outer tubing surrounding the inner sleeve wherein the distal end of the outer tubing is bonded to the distal end of the inner sleeve to form an annular soft tip cavity between the inner sleeve and outer tubing, the annular soft tip cavity being in fluid communication with the internal cavity of the balloon;
   wherein the balloon and soft tip define a combined internal cavity communicating with the fluid supply lumen, the combined internal cavity holding a first balloon volume when the balloon and the soft tip are filled with a first fluid volume; and
   (b) a build wire having a first portion disposed within the elongate shaft, a second portion disposed within the combined internal cavity, and a distal end projecting through the distal opening of the soft tip, the second portion of the build wire defining a build wire volume;
   wherein the first balloon volume consists of the first fluid volume plus the build wire volume.

2. The system of claim 1 wherein the second portion of the build wire has an outer surface in direct communication with a fluid in the combined internal cavity.

3. The system of claim 1 wherein the balloon catheter arrangement lacks an internal wire guide cannula around the second portion of the build wire.

4. The system of claim 1 further comprising:
   a wire guide having a proximal end and a distal end, the proximal end of the wire guide being adapted to form a releasable engagement with the distal end of the build wire;
   wherein the releasable engagement, the balloon, and the soft tip are adapted to permit advancement of the balloon and soft tip from the build wire over the releasable engagement onto the wire guide.

5. The system of claim 4 wherein the releasable engagement comprises a frictional engagement.

6. The system of claim 4 wherein the releasable engagement comprises a magnetic engagement.

7. The system of claim 4 wherein the releasable engagement is a threaded engagement.

8. The system of claim 4 wherein the distal end of the build wire is configured as a bore hole adapted to accept the proximal end of the wire guide.

9. The system of claim 8 wherein the bore hole is tapered.

10. The system of claim 8 wherein the bore hole has a frictive inner surface.

11. The system of claim 8 wherein the distal end of the build wire has a tapered outer surface.

12. A low profile balloon catheter system comprising:
    (a) a balloon catheter arrangement comprising
       (i) an elongate shaft having a fluid supply lumen, a proximal end, and a distal end;
       (ii) a balloon having an internal cavity, a proximal portion and a distal neck, the proximal portion of the balloon being mounted on the distal end of the elongate shaft; and
       (iii) a soft tip having a proximal end, a distal end, and a distal opening, wherein the proximal end of the soft tip is joined to the distal neck of the balloon, the soft an outer tubing having a proximal end and a distal end, the proximal end of the outer tubing being bonded to the distal neck of the balloon, the outer tubing surrounding the inner sleeve wherein the distal end of the outer tubing is bonded to the distal end of the inner sleeve to form an annular soft tip cavity between the inner sleeve and outer tubing, the annular soft tip cavity being in fluid communication with the internal cavity of the balloon, wherein the inner sleeve is adapted to form a circumferential seal around the wire guide under fluid pressure from the annular cavity;
    wherein the balloon and soft tip define a combined internal cavity communicating with the fluid supply lumen, the combined internal cavity holding a second balloon volume when the balloon and the soft tip are filled with a second fluid volume; and (b) a wire guide having a first portion disposed within the elongate shaft, a second portion disposed within the combined internal cavity, and a distal end projecting through the distal opening of the soft tip, the second portion of the wire guide defining a wire guide volume; wherein the second balloon volume consists of the second fluid volume plus the wire guide volume.

13. A system for advancing a low profile balloon catheter onto a wire guide comprising:
   (a) a balloon catheter arrangement comprising
      (i) an elongate shaft having a fluid supply lumen, a proximal end, and a distal end;
      (ii) a balloon having an internal cavity, a proximal portion and a distal neck, the proximal portion of the balloon being mounted on the distal end of the elongate shaft, the balloon lacking an internal wire guide cannula; and
      (iii) a soft tip having a proximal end, a distal end, and a distal opening, the proximal end of the soft tip being joined to the distal neck of the balloon, the soft tip further comprising an inner sleeve having a proximal end and a distal end; and an outer tubing having proximal end and a distal end, the proximal end of the outer tubing being bonded to the distal neck of the balloon, the outer tubing surrounding the inner sleeve wherein the distal end of the outer tubing is bonded to the distal end of the inner sleeve to form an annular soft tip cavity between the inner sleeve and outer tubing, the annular soft tip cavity being in fluid communication with the internal cavity of the balloon;
   wherein the balloon and soft tip define a combined internal cavity communicating with the fluid supply lumen of the elongate shaft;
   (b) a build wire having a first portion, a second portion, and a distal end; and
   (c) a wire guide having a first portion, a second portion, a proximal end, and a distal end, the proximal end of the wire guide being adapted to form a releasable engagement with the distal end of the build wire;
   the balloon catheter arrangement occupying a first position when the first portion of the build wire is disposed within the elongate shaft, the second portion of the build wire is disposed within the combined internal cavity and the distal end of the build wire projects through the distal opening of the soft tip; and
   the balloon catheter arrangement occupying a second position when the first portion of the wire guide is disposed within the elongate shaft, the second portion of the wire guide is disposed within the combined internal cavity and the distal end of the wire guide projects through the distal opening of the soft tip.

14. The system of claim 13 wherein the soft tip forms a sealing engagement around the wire guide when the balloon catheter arrangement occupies the second position and the combined internal cavity is filled with a fluid.

15. The system of claim 13 wherein the releasable engagement, the balloon, and the soft tip are adapted to permit advancement of the balloon and soft tip from the build wire over the releasable engagement onto the wire guide.

16. The system of claim 13 wherein the second portion of the build wire has an outer surface in direct communication with a fluid in the combined internal cavity when the balloon catheter arrangement occupies the first position.

* * * * *